United States Patent
Wang

(10) Patent No.: US 6,627,750 B2
(45) Date of Patent: Sep. 30, 2003

(54) HIGHLY CARBOXYLATED CELLULOSE FIBERS AND PROCESS OF MAKING THE SAME

(75) Inventor: Linfu Wang, Jesup, GA (US)

(73) Assignee: Rayonier Inc., Jacksonville, FL (US)

( * ) Notice: Subject to any disclaimer, the term of this patent is extended or adjusted under 35 U.S.C. 154(b) by 13 days.

(21) Appl. No.: 09/922,124

(22) Filed: Aug. 3, 2001

(65) Prior Publication Data

US 2003/0054167 A1 Mar. 20, 2003

(51) Int. Cl.[7] ............ C08B 3/00; C08B 3/02; C08B 3/20
(52) U.S. Cl. ............ 536/63; 536/56; 536/124; 428/364
(58) Field of Search ............ 536/56, 63, 124; 428/364

(56) References Cited

U.S. PATENT DOCUMENTS

| | | | |
|---|---|---|---|
| 3,755,297 A | 8/1973 | Campbell et al. | 260/227 |
| 4,410,694 A | 10/1983 | Nakayama et al. | 536/76 |
| 4,734,239 A | 3/1988 | Diamantoglou et al. | 264/187 |
| 5,371,211 A | * 12/1994 | Faber | |
| 5,741,901 A | 4/1998 | Cook et al. | 536/76 |
| 5,935,383 A | 8/1999 | Sun et al. | 162/158 |
| 5,973,139 A | 10/1999 | Lee et al. | 536/63 |
| 5,981,738 A | 11/1999 | Cook et al. | 536/76 |
| 6,037,466 A | 3/2000 | Maliczyszyn et al. | 536/102 |
| 6,241,853 B1 | 6/2001 | Smith et al. | 162/141 |

FOREIGN PATENT DOCUMENTS

| | | |
|---|---|---|
| WO | WO99/40120 | 8/1999 |
| WO | WO00/39389 | 7/2000 |

* cited by examiner

*Primary Examiner*—James O. Wilson
*Assistant Examiner*—Michael C. Henry
(74) *Attorney, Agent, or Firm*—Kramer Levin Naftalis & Frankel LLP

(57) ABSTRACT

Disclosed is a process for producing water-insoluble cellulose fibers having high carboxyl content by reacting cellulose fiber in suspension with dicarboxylic acid anhydride or chloride in the presence of a basic catalyst. The fibers produced possess a unique combination of high carboxyl content in the range of 100 to 4000 meq/kg, and high average viscosity, in the range of 0.5 to 12 dl/g. The carboxylated cellulose fibers according the invention can be made with a combination of carboxyl content and average viscosity which are suitable for use in numerous applications, including absorbent products, health care products, specialty papers, adhesives, detergents, biodegradable fibers, precursors for aqueous coatings and ion exchange fibers.

14 Claims, No Drawings

HIGHLY CARBOXYLATED CELLULOSE FIBERS AND PROCESS OF MAKING THE SAME

The present invention relates to highly carboxylated cellulose fibers and a process for making such fibers. The highly carboxylated cellulose fibers of the inventions are water-insoluble and have enhanced absorbency toward water and body fluids, making them desirable for use in personal hygiene articles, high strength paper making, cellulose ester coatings with low volatile organic components (VOC), as well as in many other applications. The process of the invention is based on the reaction of organic dicarboxylic acid anhydrides, such as phthalic anhydride, maleic anhydride, succinic anhydride, glutaric anhydride, trimellitic anhydride, 1,2-cyclohexanedicarboxylic anhydride, and oxalyl chloride and cellulosic fibers.

BACKGROUND OF THE INVENTION

Carboxylated cellulose fibers have been used and proposed for use in a number of applications where the presence of carboxyl groups on the fibers is believed to enhance some properties of the cellulose fibers. However, the limited extent to which cellulose fibers could heretofore be carboxylated in a cost-effective and environmentally benign fashion has limited the use of such fibers.

Polymer composites or blends employing cellulose exhibit limited compatibility with certain polymeric materials, including nylon-6 and polypropylene. This incompatibility diminishes the mechanical properties of the polymer composite or blend products. The compatibility of cellulose to such polymeric materials is improved by adding carboxylic acid groups to the cellulose, where it is believed that the carboxyl groups enhance the compatibility between polymers and cellulose.

A need also exists for water-insoluble fibers having improved absorbency towards water or body fluids such as urine, blood, mucus, menses, lymph and other body exudates. Fibers having improved absorbency would find ready application in areas such as personal hygiene, medicine, house keeping, clothing and electronics, as well as in other products. One of the most important applications of water-insoluble fibers having improved absorbency is in disposable absorbent articles, such as diapers or incontinence pads. It would be particularly desirable if articles incorporating such fibers could be processed using conventional commercial equipment. To enable such processing, improved absorbency fibers must meet certain minimal values with regard to fiber strength and fiber length.

In the art of papermaking, there are materials which are used to improve the wet strength of paper. These materials are known in the art as "wet strength agents." Cationic wet strength agents are perhaps the most widely used variety. The effectiveness of cationic wet strength agents is often limited by the low retention of the wet strength agent on conventional cellulose fibers. This low retention is frequently due to the cationic agents not finding suitable anionic sites for attachment to the fiber, which causes them to remain in solution or to be washed off the fiber after application. Although cationic promoters can be used to increase wetting agent retention, they do not increase the number of anionic sites on a fiber surface, and in some cases may actually decrease the number of such sites, thus inhibiting the wet strength agent from performing its function. It is desirable to increase the number of anionic sites on a fiber to improve the efficiency of wet strength agents. The anionic sites on conventional cellulose pulps can be measured in terms of the carboxyl group content of cellulose, which is typically in the range of about 20 to about 120 milliequivalents per kilogram (meq/kg) of cellulose. U.S. Pat. No. 5,935,383 discloses a method for improving the efficiency of aqueous cationic wet strength additives by pretreating cellulose surfaces with reactive anionic compounds, thus providing the cellulose surface with additional anionic sites suitable for retaining cationic wet strength additives on the cellulose.

Cellulose esters are often used in pharmaceuticals and industrial coatings. However, they frequently exhibit relatively low solid contents in suitable solvents, necessitating use of large amounts of solvent. The use of high solvent levels is undesirable since it is associated with prolonged drying times and atmospheric contamination through solvent evaporation. Although solvent borne cellulose esters provide desirable coatings properties, the current trend is to formulations which require reduced amounts of the volatile organic components (VOC), or which employ water soluble coating formulations, thereby entirely eliminating VOC. This trend has limited the use of solvent borne cellulose esters in coatings applications. WO99/40120 describes an attempt to make carboxylated cellulose esters having improved solvent solubility to enable high solids coating compositions. The method described in WO 99/40120 utilizes oxidized cellulose which is activated with water. The water in the activated cellulose is then displaced with acetic acid and the product esterified and then hydrolyzed. Cellulose esters using carboxylated cellulose fibers as starting material prepared according to the present invention overcome the poor solubility of conventional cellulose esters in aqueous media and thus reduce the need to use VOC in the production of coatings, for example, cellulose esters.

Cellulose fibers having high carboxyl content would be useful in all of the above applications. Carboxylated cellulose can be made through: (a) oxidation of cellulose, (b) etherification of cellulose with monochloroacetic acid, (c) esterification of cellulose with some dicarboxylic acid anhydrides or chlorides, such as phthalic anhydride, maleic anhydride, succinic anhydride and oxalyl chloride.

Some oxidants such as hypohalite, chlorine dioxide, nitrogen dioxide (dinitrogen tetraoxide), permanganate, dichromate-sulfuric acid and hypochlorous acid can be used to make carboxylated cellulose fiber; however, the obtained oxidized celluloses (or oxycelluloses) either have low carboxyl content (lower than 250 meq/kg) or very low intrinsic viscosity as measured in cupriethylenediamine (Cuene I.V.) In addition, some oxidized celluloses may contain aldehyde and/or ketone functionalities besides carboxyl group depending on the nature of the oxidant and the reaction conditions used in their preparation. This can impair their performance as coatings. Sodium (or potassium) periodate is a very effective oxidant, however, it cannot be used cost effectively because there is no viable method to recover periodate. Furthermore, carboxylated cellulose fibers made by the periodate method with carboxyl contents higher than 1000 meq/kg, have Cuene I.V. less than 2 dL/g, which limits their applications.

Etherification of cellulose by monochloroacetic acid yields carboxylated cellulose (carboxymethyl cellulose) with relatively high carboxyl content and high I.V.; however, the carboxylated cellulose products produced in this fashion are usually particles, instead of fibers, if the degree of substitution (DS) of carboxyl group is higher than 0.3. Particles are susceptible to water absorption except when present in the acid form and/or crosslinked. U.S. Pat. No.

4,410,694 discloses a method for preparing carboxylated fibers in water using monochloroacetic acid; however, the degree of substitution (DS) of the carboxylated fibers is very low.

U.S. Pat. No. 4,734,239 describes the production of water-insoluble fibers of cellulose monoesters of maleic acid, succinic acid and phthalic acid, having an high absorbability for water and physiological liquids. The carboxylated cellulose was prepared via esterification of cellulose by dicarboxylic acid in the presence of dimethylacetamide/ lithium chloride (DMAc/LiCL) as solvent and potassium acetate as catalyst. The solvent medium, DMAc/LiCL is costly to use and DMAc is toxic. Further, the carboxylated cellulose produced according to the patent is substantially dissolved and must be spun to produce a fiber.

Accordingly, there exists a need for an economical and environmentally benign method of making highly carboxylated fibers from polysaccharide fibers, including wood cellulose, which retain their fiber form during carboxylation and which have sufficient fiber strength to be processed into commercial articles, and in particular absorbent articles, utilizing conventional processing equipment.

There is also a need for biodegradable disposable articles for personal hygiene, medical and domestic use. The carboxylated cellulose fibers of the invention are suitable for use in such articles. Highly carboxylated cellulose fibers can replace, partially or totally, base fiber non-woven materials in wipes and disposable articles, and fiber/super absorbent polymer mixes in absorbent products, to make biodegradable disposable absorbent articles.

SUMMARY OF THE INVENTION

The present invention provides water-insoluble, highly carboxylated cellulose fibers which are suitable for use in cellulose acetate coatings, absorbent core materials, high wet strength papers and polymer composites. The highly carboxylated cellulose fibers of the invention retain their fiber form throughout the carboxylation process and have sufficient fiber strength and length to be processed using conventional fiber processing technology. They can be made with a wide range of intrinsic viscosities and a high degree of substitution ("DS") of carboxyl groups.

The highly carboxylated water-insoluble cellulose fibers of present invention are made by reacting cellulose with dicarboxylic acid anhydrides or chlorides using weak organic acid, and a base or basic salt. Preferably the weak organic acid acts as both a dispersing agent and induces fiber swelling while the base or basic salt acts as a catalyst. The fibers produced possess a unique combination of high carboxyl content and high intrinsic viscosity. The range of carboxyl content which can be achieved using the invention is from about 150 to greater than 4000 milliequivalents per kilogram (meq/kg). The range of viscosities achievable with the highly carboxylated cellulose fibers according to the invention is from about 0.5 dl/g to about 12 dl/g. This combination of carboxyl content and viscosity enable the carboxylated cellulose fibers of the invention to be utilized in a wide variety of applications, including absorbent products, health care products, specialty papers, adhesives, detergents, biodegradable fibers, ion exchange fibers and as precursors for aqueous coatings.

The highly carboxylated cellulose fibers of the invention can be made with any fibrous polysaccharide material, including cellulosic pulp derived from softwood pulp, such as various pines (Southern pine, White pine, Caribbean pine), Western hemlock, various spruces (e.g., Sitka Spruce), Douglas fir, from hardwood pulp sources, such as gum, maple, oak, eucalyptus, poplar, beech, or aspen, and from cotton linters, bagasse, cereal straw, reeds, kenaf, bamboo, and regenerated fibers such as rayon and lyocell, and mixtures of all of the foregoing. The cellulose fibers useful in the invention can be subjected to mechanical and/or chemical pretreatment, such as defiberization, bleaching, mercerization or chemical modification, prior to carboxylation.

In accordance with the invention a suitable cellulose fiber having an average Cuene I.V. in the range of from about 2 to about 15, and preferably in the range of from about 3 to about 13, is:

(a) dispersed in an weak organic acid to form a suspension having a consistency of about 0.5% to about 20% by weight, and preferably about 1% to about 15% by weight, at a temperature from about 15° C. to about 60° C., and preferably at about 20° C. to about 50° C.;

(b) the obtained suspension of cellulose and weak organic acid is reacted with a dicarboxylic acid anhydride or an anhydrous dicarboxylic acid chloride in a mole ratio from about 0.1:1.0 to 10:1.0 (dicarboxylic acid anhydride or chloride : cellulose), and preferably in a mole ratio of about 0.5:1.0 to about 5:1.0, at about 50° C. to about 118° C., and preferably from about 60° C. to about 100° C., in the presence of a basic catalyst, over a period from about 0.3 hours to about 15.0 hours, and preferably from about 0.5 hours to about 12.0 hours, and most preferably from about 2.0 hours to about 8.0 hours, to obtain carboxylated cellulose fibers; and (c) the produced carboxylated cellulose fibers are separated from the reaction suspension by filtering, or centrifuging, or other separation method.

Where necessary or helpful, such as for fibers intended for absorbent material application, the carboxylated cellulose fibers of the invention can be partially or completely converted into the corresponding fiber-shaped salts by direct reaction with alkali metal hydroxide, carbonate, acetate, alkali metal alcoholates, ammonia or primary or secondary amine.

It is essential for obtaining carboxylated fibers with satisfactory mechanical characteristics that the fibers have sufficiently high degree of polymerization. It is therefore essential that the starting polysaccharide fibers display an average Cuene I.V. from 3.0 to 13.0, preferably from 4.0 to 13.0, which should be substantially maintained upon the reaction with dicarboxylic acid anhydrides or chlorides. The starting materials can be wood cellulose pulps including hard wood pulp and soft wood pulp, non-wood pulp such as cotton linter, bagasse or cereal straw or regenerate fiber such as Rayon and lyocell. The starting material can be also other polysaccharides such as starch, chitin, chitosan or pullulan.

The esterifying reagent can be a dicarboxylic acid anhydride such as phthalic anhydride, maleic anhydride, poly (maleic anhydride), succinic anhydride, glutaric anhydride or a dicarboxylic acid chloride, such as oxalyl chloride. The esterifying reagent can also be 1,2,4-benzenetricarboxylic anhydride, 1,2-cyclohexanedicarbocylic anhydride or mixtures of all of the foregoing. The esterifying reagents useful in the invention have the below general structures:

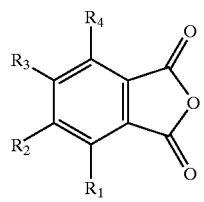

FIG. 1 wherein $R_1$, $R_2$, $R_3$, $R_4$=H, alkyl, aryl, halogen, carboxyl, carboxyalkyoxyl or amide; and

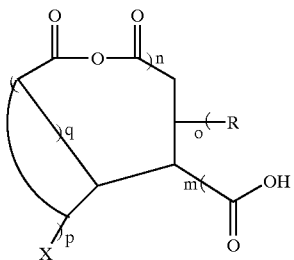

FIG. 2 wherein R=alkyl or aryl; X=halogen, —CN or CONH2; and $m \geq 0$, $n \geq 1$, $o \geq 0$, $p \geq 0$ and $q \geq 0$.

Generally, the esterifying reagents are employed in amounts from 10 to 1000% by weight relative to the starting cellulose fiber, depending on the carboxyl content of product needed. To avoid the hydrolysis of esterifying reagents and the degradation of cellulose, a weak acid dispersant, such as acetic acid or other organic acid, must be used. The reaction temperature and reaction periods must be adjusted relative to each other. Reaction temperatures of from about 50° C. to 130° C., and preferably about 60° C. to about 118° C., with reaction times of about 0.3 hours to about 15 hours, and preferably 0.5 hours to about 12 hours, are believed to yield carboxylated cellulose esters of the invention having desirable properties. Reaction temperatures from 70° C. to 118° C. and reaction times from 2 to 5 hours have proven to be particularly advantageous for the reaction of the invention.

Various acids are well known catalysts for the esterification reaction. Unexpectedly these acids are not suitable for the reaction of cellulose and dicarboxylic acid anhydride, as they not only result in fibers having low intrinsic viscosities and/or products not having a fiber shape, but also because of the low carboxyl content of the products made with them. However, basic esterification catalysts are well suitable for cellulose esterification reactions of the invention, especially suitable are those catalysts that minimize the degradation of the cellulose. By way of example, the following tertiary amines are useful in the present invention 4-N,N-dimethylaminopyridine, collidin, pyridine and triethylamine. Preferred as esterification catalysts are basic salts of monocarboxylic acids, such as sodium acetate, potassium acetate, sodium propionate, potassium propionate, sodium butyrate and potassium butyrate. Generally, these basic salts are employed in amounts from about 0 (i.e., not present) to about 150% by weight, and preferably from about 5% to about 50% by weight, and most preferably from about 10% to about 20% by weight, relative to the cellulose fibers treated.

The obtained carboxylated cellulose fibers can be characterized by solid state $C^{13}$ NMR, Cuene I.V. measurement, and carboxyl content measurement using a conductometric titration method.

A diaper incorporating the carboxylated fiber according to the invention comprises: (a) a liquid impervious backing sheet; (b) a relatively hydrophobic, liquid pervious topsheet; (c) a flexible absorbent core positioned between said backing sheet and the topsheet. The flexible absorbent core comprises of hydrophilic fiber material and optionally particles of a substantially water-insoluble hydrogel material, known as a super absorbent polymer (SAP). The highly carboxylated polysaccharide ester fibers of the invention can replace, partially or totally, the super absorbent polymer conventionally used in many absorbent articles.

The carboxylated cellulose fibers of the invention can also be used in feminine hygiene articles and other articles wherein absorbent fibers find application. The structure and method of fabrication for such articles are well known to those skilled in the art of the invention.

The advantage of the present invention is that it does not require toxic solvents and does not require spinning technology to produce a fibrous material.

DESCRIPTION OF THE PREFERRED EMBODIMENTS

EXAMPLE 1

In a three-necked reaction kettle of volume 2 liter, 18.5 g cellulose (Rayonier, Ethenier-UHV, available from Rayonier Performance Fibers Division of Jesup, Ga.; having Cuene I.V.=12.5 and approximately 92% oven dryness (OD)) was suspended in 365 ml of acetic acid. After 10 minutes stirring at room temperature, 51 g of succinic anhydride and 25.5 g of sodium acetate trihydrate were added. The temperature then was gradually raised to 80° C. over a period of 1 hour and the reaction was carried out at this temperature for 8 hours. The reaction mixture was filtered and the obtained carboxylated cellulose fibers were washed with distilled water 5 times and prepared into a handsheet. The handsheet was air dried at a temperature below 50° C. before taking Cuene I.V. and carboxyl content measurements. The cellulose succinate fibers obtained in this manner displayed the following characteristics:

| Sample | Cuene I.V. | Carboxyl content (meq/kg) |
|---|---|---|
| Ethenier-F-UHV (control) | 12.5 | 70 |
| 1 | 8.87 | 773 |

EXAMPLE 2

Cellulose succinic acid ester was produced according to the same process described in Example 1, except the starting cellulose pulp was mercerized Ethenier-UHV, available from Rayonier Performance Fibers Division (Jesup, Ga.). The mercerized fiber was prepared by treating the Ethenier-UHV pulp with 16% sodium hydroxide solution at 10% consistency, for 15 minutes at room temperature and washing the product with distilled water 5 times prior to drying. The carboxylated pulp had a Cuene I.V.=5.34 and carboxyl content of 1280 meq/kg.

EXAMPLES 3–5

In a three-necked reaction kettle of volume 2 liter, 64.0 g of cellulose (Rayonier, Sulfatate-H-J, available from Rayonier Performance Fibers Division of Jesup, Ga.; having a Cuene I.V. of 8.13 units and approximately 92% OD) was suspended in 1200 ml of acetic acid. The suspension was stirred for 10 minutes at room temperature and then 320 g of succinic anhydride (Example 3) and 12.8 g of sodium acetate were added to it. The temperature of the suspension then was gradually raised to 80° C. over a period of 1 hour and the reaction carried out at this temperature for 5 hours. The reaction mixture was filtered and the obtained carboxylated cellulose fibers were washed with distilled water 5 times and prepared into handsheets. The handsheets were air dried below 50° C. before taking Cuene I.V. and carboxyl content measurements.

The procedure for Examples 4 and 5 were the same as Example 3 except that the esterifying reagent used were maleic anhydride (Example 4) and phthalic anhydride (Example 5.) The cellulose phthalate and maleate fibers obtained in this manner displayed the following characteristics:

| Sample | Esterifying reagent | Cuene I.V. | Carboxyl content (meq/kg) |
|---|---|---|---|
| 3 | succinic anhydride | 4.37 | 2210 |
| 4 | maleic anhydride | 2.82 | 1620 |
| 5 | phthalic anhydride | 4.84 | 763 |

EXAMPLES 6–7

In a three-necked reaction kettle of volume 2 liter, 20.0 g of cellulose (Rayonier, Sulfatate-H-J, with Cuene I.V.=8.13 units and approximately 92% OD) was suspended in 365 ml of acetic acid. After 10 minutes stirring at room temperature, a mixture of 10 g of maleic anhydride and 10 g of phthalic anhydride, with 2.0 g of sodium hydroxide were added. The temperature of the suspension then was gradually raised to 80° C. over a period of 1 hour and the reaction carried out at this temperature for 4 hours. The reaction mixture was then filtered. The obtained carboxylated cellulose fibers were washed with distilled water 5 times and prepared into handsheets. The handsheets were air dried below 50° C. before measurement of their Cuene I.V. and carboxyl content. The procedure of Example 6 was followed for Example 7, except that the esterifying reagent in Example 7 was 20 g of glutaric anhydride. The carboxylated cellulose fibers obtained in this manner displayed the following characteristics:

| Sample | Esterifying reagent | Cuene I.V. | Carboxyl content (meq/kg) |
|---|---|---|---|
| 6 | succinic anhydride/ maleic anhydride | 2.88 | 593 |
| 7 | glutaric anhydride | 4.99 | 167 |

EXAMPLES 8–9

In a three-necked reaction kettle of volume 2 liter, 17.0 g of cellulose (Rayonier, Rayfloc-J; with Cuene I.V.=8.39 units) was suspended in 365 ml of acetic acid. After 10 minutes stirring at room temperature, 51 g of phthalic anhydride (Example 5) and 25.5 g of sodium acetate trihydrate were added. The temperature was gradually raised to 80° C. over a period of 1 hour and the reaction carried out at this temperature for 8 hours. The reaction mixture was then filtered. The obtained carboxylated cellulose fibers were washed with distilled water 5 times and prepared into handsheets. The handsheets were air dried below 50° C. before taking Cuene I.V. and carboxyl content measurements. The procedure of Example 8 was repeated for Example 9, except that the esterifying reagent used was maleic anhydride. The cellulose phthalate and maleate fibers obtained in this manner displayed the following characteristics:

| Sample | Esterifying reagent | Cuene I.V. | Carboxyl content (meq/kg) |
|---|---|---|---|
| Rayfloc-J (control) | | 8.39 | 103 |
| 8 | phthalic anhydride | 7.05 | 620 |
| 9 | maleic anhydride | 6.26 | 657 |

EXAMPLE 10

In a three-necked reaction kettle of volume 2 liter, 10.0 g of cellulose (Rayonier, Rayfloc-J; Cuene I.V.=8.39 units) was suspended in 265 ml of acetic acid. After 10 minutes stirring at room temperature, 100 ml of acetic acid containing pre-dissolved 5 g of poly (maleic anhydride) and 1.0 g of sodium acetate was added to the suspension. The temperature of the suspension was gradually raised to 80° C. over a period of 1 hour and the reaction carried out at this temperature for 8 hours. The reaction mixture was filtered and the obtained carboxylated cellulose fibers were washed with distilled water 5 times and prepared into handsheets. The handsheets were air dried below 50° C. before taking Cuene I.V. and carboxyl content measurements. The carboxyl content of the obtained product was 1250 meq/kg. A Cuene IV value could not be obtained because the product would not dissolve in Cuene solvent.

EXAMPLES 11–15

The cellulose phthalate were prepared for Examples 11–15 using the method of Example 8, except for the catalyst type and amount which were as set forth below. The obtained products displayed the following characteristics:

| Sample | Catalyst/pulp ratio | Cuene I.V. | Carboxyl content (meq/kg) |
|---|---|---|---|
| Rayfloc-J (control) | | 8.39 | 103 |
| 11 | 1.5/1 (sodium acetate trihydrate) | 7.05 | 620 |
| 12 | 0.5/1 (sodium acetate trihydrate) | 6.32 | 737 |
| 13 | 0.1/1 (sodium acetate trihydrate) | 6.54 | 767 |
| 14 | 0/1 (none) | 5.02 | 273 |
| 15 | 0.05/1 (sulfuric acid) | 1.90 | 163 |

EXAMPLES 16–18

In a three-necked reaction kettle of volume 2 liter, 17.0 g of cellulose (Rayonier, Rayfloc-J; Cuene I.V.=8.39 units) was suspended in 365 ml of acetic acid. After 10 minutes stirring at room temperature, 8.5 g of phthalic anhydride and 1.7 g of sodium acetate trihydrate were added to the suspension. The temperature of the suspension was gradually raised to 80° C. over a period of 1 hour and the reaction carried out at this temperature for either 2 hours (Example 16), 4 hours (Example 17), or 8 hours (Example 18). The reaction mixture was filtered and the obtained carboxylated cellulose fibers from each reaction washed with distilled water 5 times and prepared into handsheets. The handsheets were air dried below 50° C. before taking Cuene I.V. and carboxyl content measurements. The cellulose phthalate fibers obtained in this manner displayed the following characteristics:

| Sample | Reaction time (h) | Cuene I.V. | Carboxyl content (meq/kg) |
|---|---|---|---|
| Rayfloc-J (control) | | 8.39 | 103 |
| 16 | 2 | 7.39 | 270 |
| 17 | 4 | 7.18 | 285 |
| 18 | 8 | 7.05 | 320 |

EXAMPLES 19–21

In a three-necked reaction kettle of volume 2 liter, 17.0 g of cellulose (Rayonier, Rayfloc-J; Cuene I.V.=8.39 units) was suspended in 365 ml of acetic acid. After 10 minutes stirring at room temperature, 8.5 g of phthalic anhydride and 1.7 g of sodium acetate trihydrate were added to the suspension. The temperature of the suspension was gradually increased to the selected reaction temperature over a period of 1 hour. The reactions were carried out at the following reaction temperatures: 55° C. (Example 19), 80° C. (Example 20) and 118° C. (Example 21), all for 2 hours. The reaction mixture was filtered and the obtained carboxylated cellulose fibers washed with distilled water 5 times and prepared into handsheets. The handsheets were air dried below 50° C. before taking Cuene I.V. and carboxyl content measurements. The cellulose phthalate fibers obtained in this manner displayed the following characteristics:

| Sample | Reaction temperature (° C.) | Cuene I.V. | Carboxyl content (meq/kg) |
|---|---|---|---|
| Rayfloc-J (control) | | 8.39 | 103 |
| 19 | 55 | 8.01 | 147 |
| 20 | 80 | 7.39 | 270 |
| 21 | 118 | 7.18 | 277 |

EXAMPLES 22–24

In a three-necked reaction kettle of volume 2 liter, 17.0 g of cellulose (Rayonier, Rayfloc-J; with Cuene I.V.=8.39 units) was suspended in 365 ml of acetic acid. After 10 minutes stirring at room temperature, phthalic anhydride was added to the suspension in quantities of either 34 g (Example 22), 17 g (Example 23) or 8.5 g (Example 24) along with 1.7 g of sodium acetate trihydrate. The temperature was gradually raised to 80° C. over a period of 1 hour and the reaction carried out at this temperature for 2 hours. The reaction mixture was filtered and the obtained carboxylated cellulose fibers were washed with distilled water 5 times and prepared into handsheets. The handsheets were air dried below 50° C. before taking Cuene I.V. and carboxyl content measurements. The cellulose phthalate fibers obtained in this manner displayed the following characteristics:

| Sample | phthalic anhydride/pulp ratio | Cuene I.V. | Carboxyl content (meq/kg) |
|---|---|---|---|
| Rayfloc-J (control) | | 8.39 | 103 |
| 22 | 2/1 | 7.04 | 527 |
| 23 | 1/1 | 7.38 | 367 |
| 24 | 0.5/1 | 7.39 | 270 |

EXAMPLES 25–29

In a three-necked reaction kettle of volume 2 liter, 17.0 g of 5 different polysaccharides, namely, Hardwood pulp Sulfatate-H-J-EE (Example 25), Softwood pulp Rayonier Placetate-F (Example 26), both from Rayonier Performance Fibers Division (Jesup, Ga.), Rayon fiber (Example 27), corn starch (Example 28) and cotton linter (Example 29) were suspended in 365 ml of acetic acid. After 10 minutes stirring at room temperature, 8.5 g of phthalic anhydride and 1.7 g of sodium hydroxide were added to each suspension. The temperature of each suspension was gradually raised to 80° C. over a period of 1 hour and the reaction carried out at this temperature for 4 hours. The reaction mixtures were filtered and the obtained carboxylated cellulose fibers from Examples 25–29 washed with distilled water 5 times and then prepared into handsheets. The handsheets were air dried below 50° C. before taking Cuene I.V. and carboxyl content measurements. The cellulose phtalate fibers obtained in this manner displayed the following characteristics:

| Sample | Polysaccharide | Cuene I.V. | Carboxyl content (meq/kg) |
|---|---|---|---|
| 25 | Sulfatate-HJ-EE | 4.45 | 320 |
| 26 | Placetate-F | 5.96 | 367 |
| 27 | Rayon fibers | 2.29 | 303 |
| 28 | Corn starch | 1.48 | 550 |
| 29 | Cotton linter | 2.88 | 270 |

The invention has been illustrated, and described, as embodied in water-insoluble fibers of cellulose esters of dicarboxylic acids. However, the process and products of the invention are not intended to be limited to the specific examples shown, since various modifications and changes may be made thereto without departing from the spirit of the present invention.

What is claimed is:

1. A process for the making of water-insoluble carboxylated polysaccharide fibers comprising:
   (a) dispersing polysaccharide fibers in organic acid to form a fiber suspension having a fiber consistency of about 0.5% to about 20% by weight.
   (b) adding a dicarboxylic acid anhydride or anhydrous dicarboxylic acid chloride to said fiber suspension in a mole ratio to said polysaccharide fiber of from about 0.1:1.0 to about 10.0:1.0 to form a reaction mixture and reacting said mixture at about 50° C. to about 118° C. in the presence of a basic catalyst for a time sufficient to obtain carboxylated polysaccharide fibers.

2. The process according to claim 1, wherein said polysaccharide fiber is a hardwood cellulose pulp, a softwood cellulose pulp, cotton linters, bagasse, cereal straw, reeds, kenaf, bamboo, rayon, lyocell, other regenerated cellulose, starch, chitin, chitosan, pullulan or mixtures thereof.

3. The process according to claim 1, wherein said organic acid is acetic acid, propionic acid, butyric acid, glutaric acid or oxalic acid.

4. The process according to claim 1, wherein said reaction mixture is reacted for a period from about 0.3 hours to about 15 hours.

5. The process according to claim 1, wherein said suspension has a fiber consistency of about 1.0% to about 15% by weight, said dicarboxylic acid anhydride or anhydrous dicarboxylic acid chloride is added to said polysaccharide fiber suspension in a mole ratio of from about 0.5:1.0 to about 5:1.0; and said reaction mixture is reacted at about 60° C. to about 118° C.

6. The process according to claim number 5, wherein said suspension has a fiber consistency of about 2% to about 10% by weight, said dicarboxylic acid anhydride or anhydrous dicarboxylic acid chloride is added to said polysaccharide fiber suspension in a mole ratio of from about 1.0:1.0 to about 5:1.0, and said reaction mixture is reacted at about 60° C. to about 118° C. for a period of from about 0.5 hours to about 12 hours.

7. The process according to claim number 6, wherein said reaction mixture is reacted for a period from about 2 hours to about 8 hours.

8. The process according to claim 1, wherein said dicarboxylic acid anhydride or said anhydrous dicarboxylic acid chloride are selected from the group consisting of phthalic anhydride, 1, 2, 4-benzenetricarboxylic anhydride, maleic anhydride, poly(maleic anhydride), succinic anhydride, glutaric anhydride, 1,2-cyclohexanedicarbocylic anhydride and oxalic acid chloride and mixtures thereof.

9. The process according to claim 1, wherein said dicarboxylic acid anhydride or said anhydrous dicarboxylic acid chloride have the below structure:

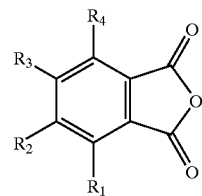

wherein $R_1$, $R_2$, $R_3$, $R_4$=H, alkyl, aryl, halogen, carboxy, carboxyalkyoxyl or amide.

10. The process according to claim 1, wherein said polysaccharide fibers are dispersed in acetic acid.

11. The process according to claim 10, wherein said reaction takes place at a reaction temperature from about 60° C. to about 118° C.

12. The process according to claim 1, wherein said basic catalyst is selected from the group consisting of alkali metal acetates, carbonates, alkali metal hydroxides, alkali metal alcoholates, ammonia, primary amines, secondary amines or mixtures thereof.

13. The process according to claim 12, wherein said basic catalyst is present in an amount, relative to the amount of said polysaccharide fiber, in the range of about 5% to about 50% by weight.

14. The process according to claim 1, wherein said carboxylated polysaccharide fibers are recovered from said reaction mixture by filtering or centrifuging.

* * * * *